US00PP19806P3

(12) United States Plant Patent
Embree et al.

(10) Patent No.: US PP19,806 P3
(45) Date of Patent: Mar. 10, 2009

(54) APPLE TREE NAMED 'MASONOVA'

(50) Latin Name: *Malus dimestica*
Varietal Denomination: Masonova

(75) Inventors: Charles G. Embree, Port Williams (CA); A. David Crowe, Wolfville (CA)

(73) Assignee: Her Majesty The Queen In Right of Canada, as represented by The Minister of Agriculture and Agri-Food, Kentville, Nova Scotia (CA)

( * ) Notice: Subject to any disclaimer, the term of this patent is extended or adjusted under 35 U.S.C. 154(b) by 0 days.

(21) Appl. No.: 11/725,127

(22) Filed: Mar. 15, 2007

(65) Prior Publication Data

US 2008/0229458 P1 Sep. 18, 2008

(51) Int. Cl.
*A01H 5/00* (2006.01)

(52) U.S. Cl. ..... Plt./161
(58) Field of Classification Search ..... Plt./161
See application file for complete search history.

(56) References Cited

FOREIGN PATENT DOCUMENTS

CA 02-3089 10/2004

OTHER PUBLICATIONS

Agriculture and Agri–Food Canada; "Cultivar Development–Apple Breeding at AAFC"; Mar. 16, 2005 (7 pages total). http://web.archive.org/web/20050316102556/http://www.agr.gc.ca/malus/breeding_e.html.*

* cited by examiner

*Primary Examiner*—Annette H Para
*Assistant Examiner*—S. B. McCormick Ewoldt
(74) *Attorney, Agent, or Firm*—Klarquist Sparkman, LLP

(57) ABSTRACT

A new apple variety distinguished by resistance to apple scab; good cold storage ability; desirable eating characteristics including soft and fine textured ivory colored flesh with some green and red venation surrounding the core, and flesh exhibiting absent to very weak browning after cutting; and the skin has solid, complete red coloration.

10 Drawing Sheets

Latin name of the genus and species of the plant claimed: *Malus domestica* Borkh.
Variety denomination: 'Masonova'.

BACKGROUND OF THE INVENTION

The present invention relates to a new and distinct variety of apple tree named 'Masonova'. The new tree 'Masonova' (experimental designation S47-24-42) resulted from a planned hybridization programme and is a selection from a cross between the pollen parent 'Empire' (unpatented) and the seed parent 'S21-42-69' (unpatented) in 1974. The cultivar 'Empire,' which is a cross between McIntosh (unpatented) and Red Delicious (unpatented), was released in Geneva, N.Y., in 1966. 'Empire' is a cultivar that gained wide commercial acceptance for a number of reasons including productivity under a wide range of planting systems, harvest during the gap between McIntosh and Red Delicious; resistance to preharvest fruit drop and storage scald, low susceptibility to fire blight, and fruit quality with respect to color, firmness, and storage. The resulting tree was selected when growing in a cultivated area in Nova Scotia, Canada.

More specifically, pollen was collected from the cultivar 'Empire', stored and dried for use in the traditional crossing method. At the full bloom stage, the emasculated flowers of 'S21-42-69' were pollinated with the dried pollen from 'Empire'. Seeds were collected from successfully pollinated fruit in the fall of 1974. In 1978, trees were planted in the seeding evaluation field block in Kentville, Nova Scotia. Fruit was evaluated from 1984 to 1988 and re-propagation for field evaluations was done in 1991.

The selection of 'Masonova' took place in 1989. Selection criteria for 'Masonova' included scab resistance, combined with the desirable eating quality traits of 'Empire' and solid, complete red coloration of the fruit.

Trees of 'Masonova' were compared to 'Novaspy' (unpatented) and 'Liberty' (unpatented) apple varieties, referred to herein as the "reference varieties." 'Novaspy' originated at AAFC as a cross between 'Nova Easygro' (unpatented)×(Red Spy×Golden Delicious, both unpatented), while 'Liberty' originated in Geneva, N.Y., as a cross between 'Macoun'×Purdue 54-12 (both unpatented).

The comparative tests and trials for 'Masonova' were conducted in 2003 and 2004. The fruit and tree characteristics were evaluated on trees planted in 1992 in a cooperative scab-resistant cultivar trial. The trial consisted of four trees of each variety grafted on 'Budogovsky 490' (unpatented) rootstock. They were planted twelve feet apart in rows which were spaced at eighteen feet.

Asexual reproduction shows that the distinguishing characteristics of 'Masonova' are established and transmitted through succeeding asexual propagations. Progeny was first asexually propagated in 1991 in Kentville, Nova Scotia.

SUMMARY OF THE INVENTION

The 'Masonova' variety is distinguished from other apple varieties due to the following unique combination of characteristics: resistance to apple scab; good cold storage ability; desirable eating characteristics including soft and fine textured ivory colored flesh with some green and red venation surrounding the core, and flesh exhibiting absent to very weak browning after cutting; the skin has solid, complete red coloration. Tree shape is upright with a spur type growth habit. Fruit shape is flat, globose with a pronounced eye basin and stalk cavity. Petal shape is orbicular.

'Masonova' is a spur-type tree with a higher density of spurs and more upright than S21-42-69 (seed parent). The fruit are generally larger and not as uniform or round. Fruit color is dark red and ground color is less green. 'S21-42-69' is a seedling that was selected for scab resistance as a replacement for McIntosh. The harvest season and color for 'Empire' is 5–10 days prior to Red Delicious, the color is predominately dark red blush over a green ground color.

A few compared characteristics of 'Empire' to 'Masonova' are as follows:

Empire

Origin: Cross between McIntosh and Delicious in 1945.

Tree: Productive, large, vigorous, upright, spreading, semi-spur type, round-topped and dense canopy.

Fruit: Average ripening date October $10^{th}$, medium sized and distinctly uniform, thick, tough skin, very dark red in color and striped. Flesh is whitish cream in color, firm, crisp and juicy. (Way, D. R., 1971, APPLE CULTIVARS. Introduced by the N.Y.S.A.E.S., 1914–1968 Search Agriculture, Vol. 1, No. 2. New York State Ag, Exp. Stn. 23–24).

'Masonova'

Origin: Cross between 'S21-42-69' and 'Empire' in 1974.

Tree: Heavy bearing tree, moderate vigor, upright, vase-shaped spreading, spur type growth habit and semi-open canopy.

*Fruit.*—Average ripening date October $10^{th}$, medium sized and uniform, surface is smooth and waxy, dark red in color with a striped blush pattern. Flesh is ivory with some green and red venation, mild sweet taste with moderate crispness.

Asexual reproduction of this new variety by grafting and budding onto 'Budogovsky 490' (unpatented) rootstock shows that the foregoing and other characteristics come true to form, are firmly fixed, and are established and transmitted through succeeding propagations.

The original 'Masonova' crosses were conducted in 1974. Seeds produced from these crosses were planted in 1978. The following detailed description concerns the original tree (S47-24-42), selected in 1989, and progeny first asexually propagated in 1991.

The original tree and progeny have been observed growing in a cultivated area in Nova Scotia, Canada. Certain characteristics of this variety, such as growth and color, may change with changing environmental conditions (e.g., light, temperature, moisture, nutrient availability, or other factors). Color descriptions and other terminology are used in accordance with their ordinary dictionary descriptions, unless the context clearly indicates otherwise. Color designations are made with reference to The Royal Horticultural Society (R.H.S.) Colour Chart. All color characteristics were determined using the 1986 version of The Royal Horticultural Society (R.H.S.) color charts and measured characteristics were based on ten plant measurements. It should be understood that the colors may vary, depending on factors such as growing and lighting conditions.

BRIEF DESCRIPTION OF THE DRAWINGS

The 'Masonova' apple is illustrated by the accompanying color photographs, in which.

The colors of an illustration of this type may vary with lighting and other conditions, therefore, color characteristics of this new variety should be determined with reference to the observations described herein, rather than from these illustrations alone.

DETAILED DESCRIPTION

'Masonova' is a mid-season dessert apple variety having a moderately good fruit setting with winter hardiness to Canadian zone 5b. 'Masonova' is resistant to scab (*Iventuria inaequalis*) and may be suitable for farming using organic growing techniques. The preferred method of propagation is budding onto rootstock liners in a nursery, although other suitable asexual growing methods may be used.

BOTANICAL

The following detailed description of the 'Masonova' variety is based on observations of asexually reproduced progeny. The observed progeny are trees which were 12 years of age and growing on 'Budogovsky 490' rootstock in Nova Scotia, Canada.

Scientific name: *Malus domestica* Borkh. 'Masonova'.

Parentage:

*Seed parent.*—'S21-42-69'.

*Pollen parent.*—'Empire'.

Tree:

*Vigor.*—Moderate.

*Overall shape.*—Upright.

*Height.*—About 14–18 ft.

*Width.*—Overall spread of about 12 ft.

*Caliper.*—Trunk cross-sectional area (TCA) $cm^2$=100 $cm^2$. TCA is the most common measurement to estimate tree size and, indirectly, the capacity of that tree to produce fruit. TCA can be estimated indirectly by using a simple tape measure and calculating the cross-section or TCA can be provided directly using a tree caliper.

Figure 1:
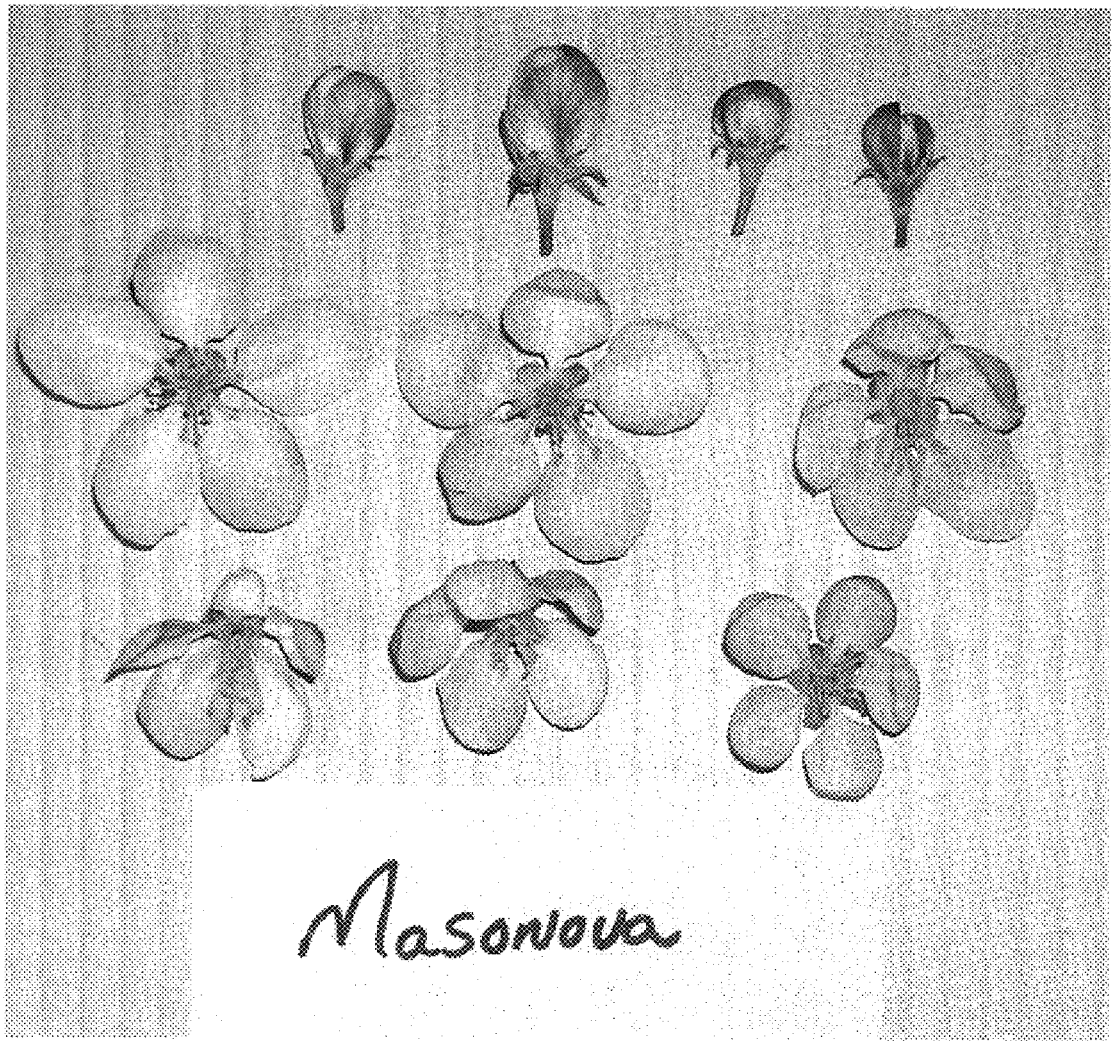
FIG. 1 shows 'Masonova' flower buds and flowers.
Figure 2:
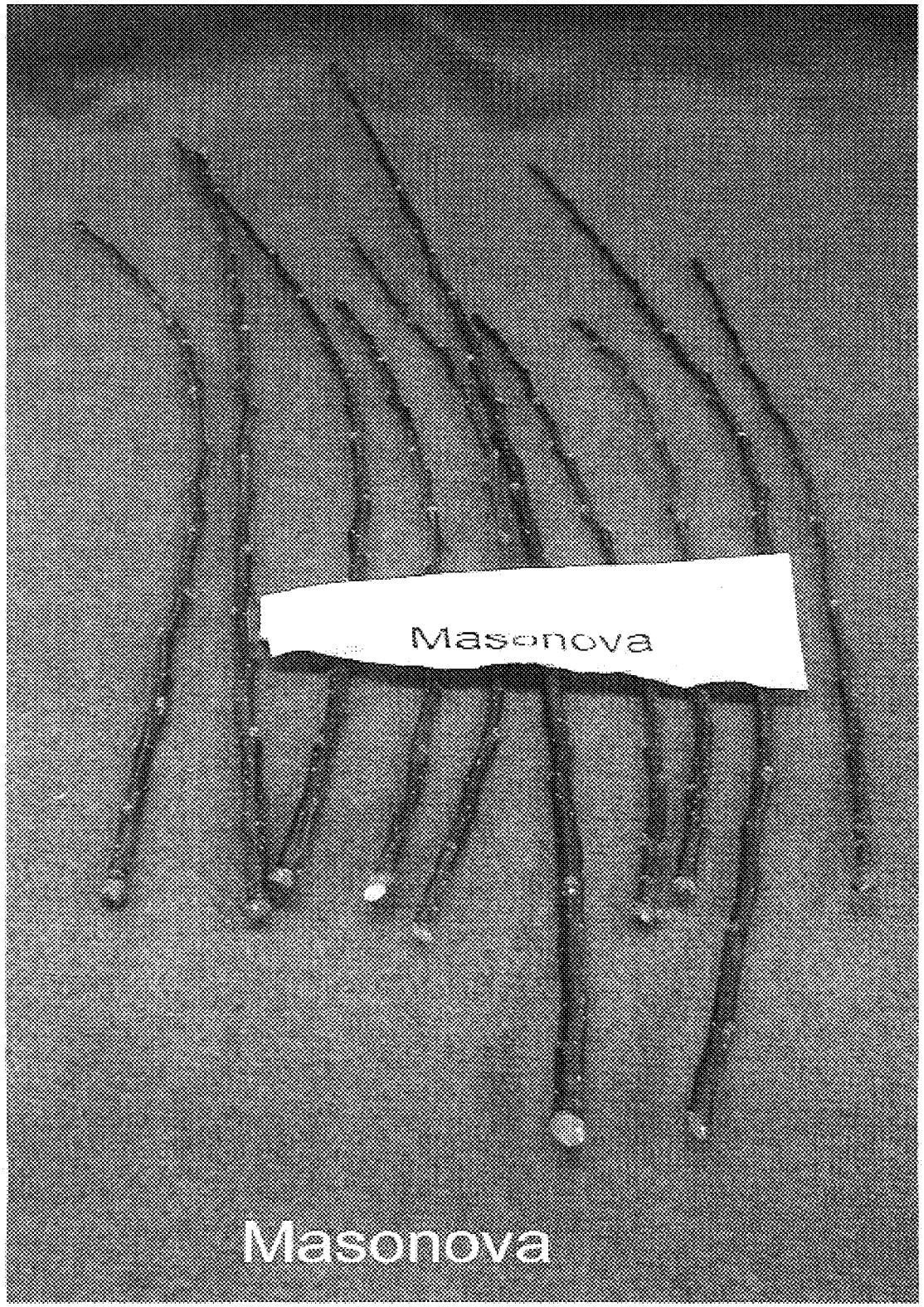
FIG. 2 shows one-year old 'Masonova' shoots.
Figure 3:
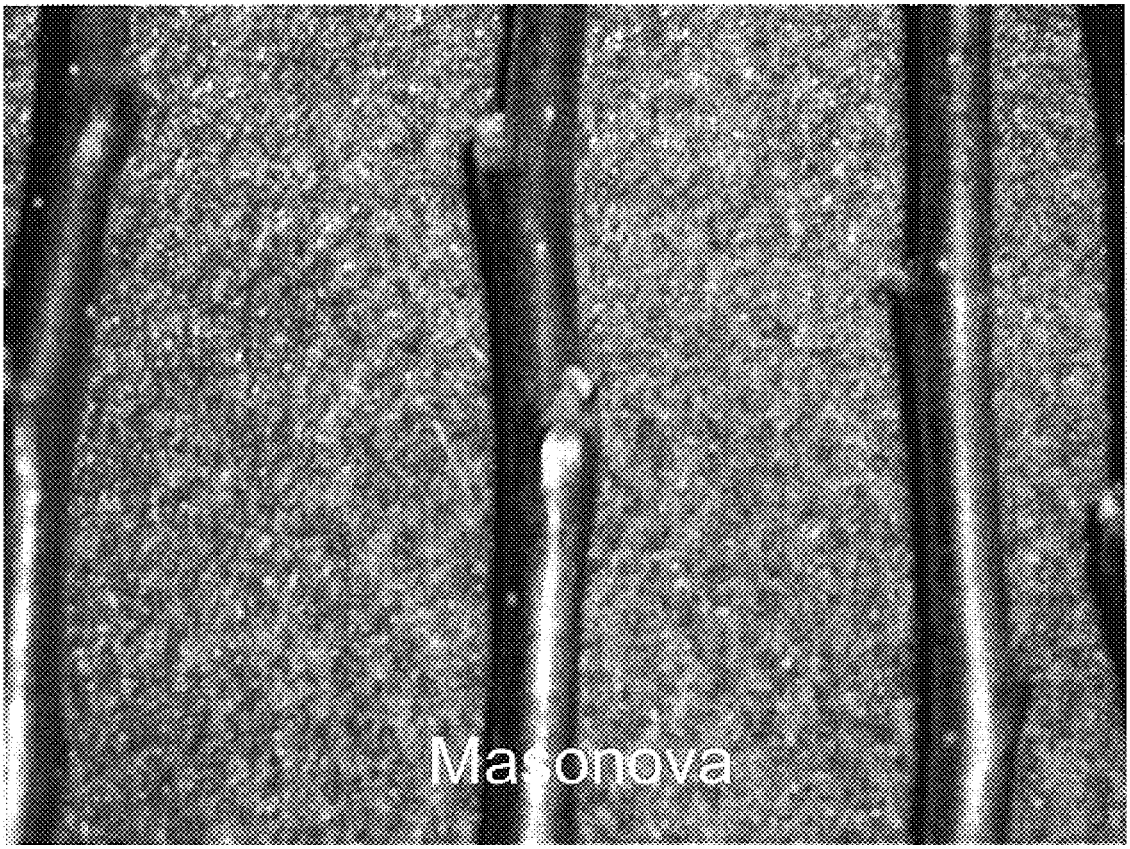
FIG. 3 shows a close-up view of a one-year old 'Masonova' shoot.
Figure 4:
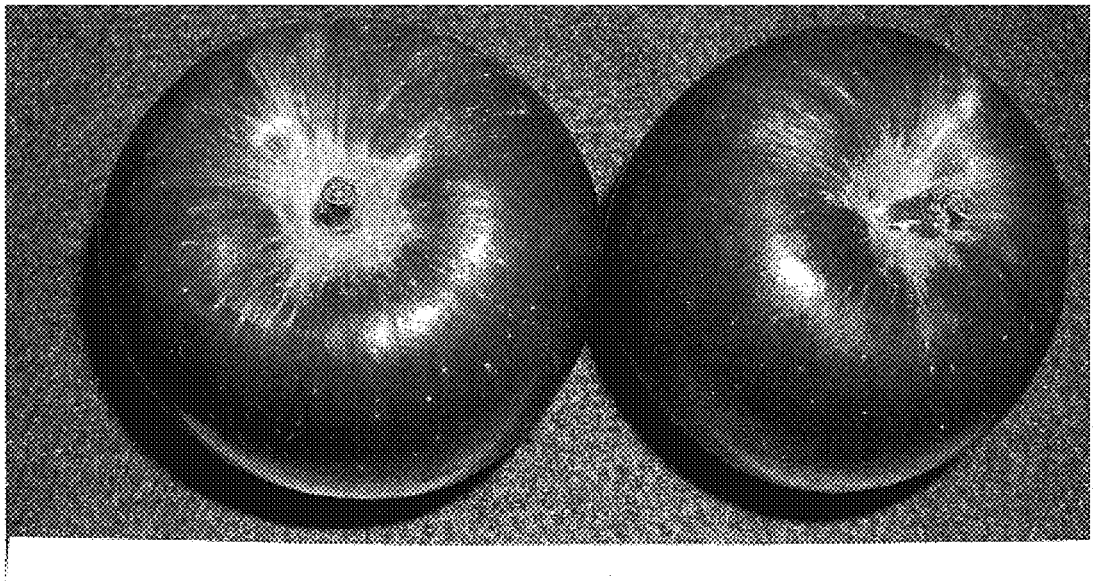
FIG. 4 shows a stem-view of two 'Masonova' apples.
Figure 5:
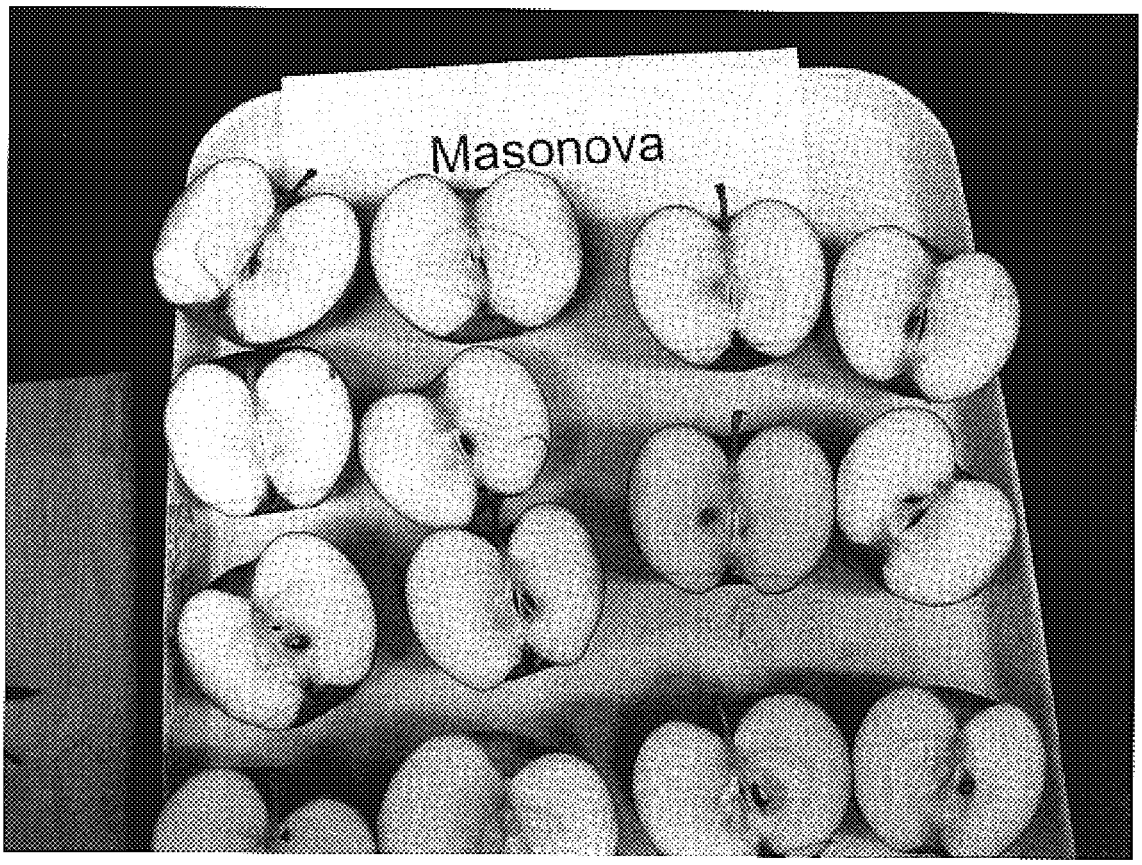
FIG. 5 shows cross-sectional views of 'Masonova' apples.
Figure 6:
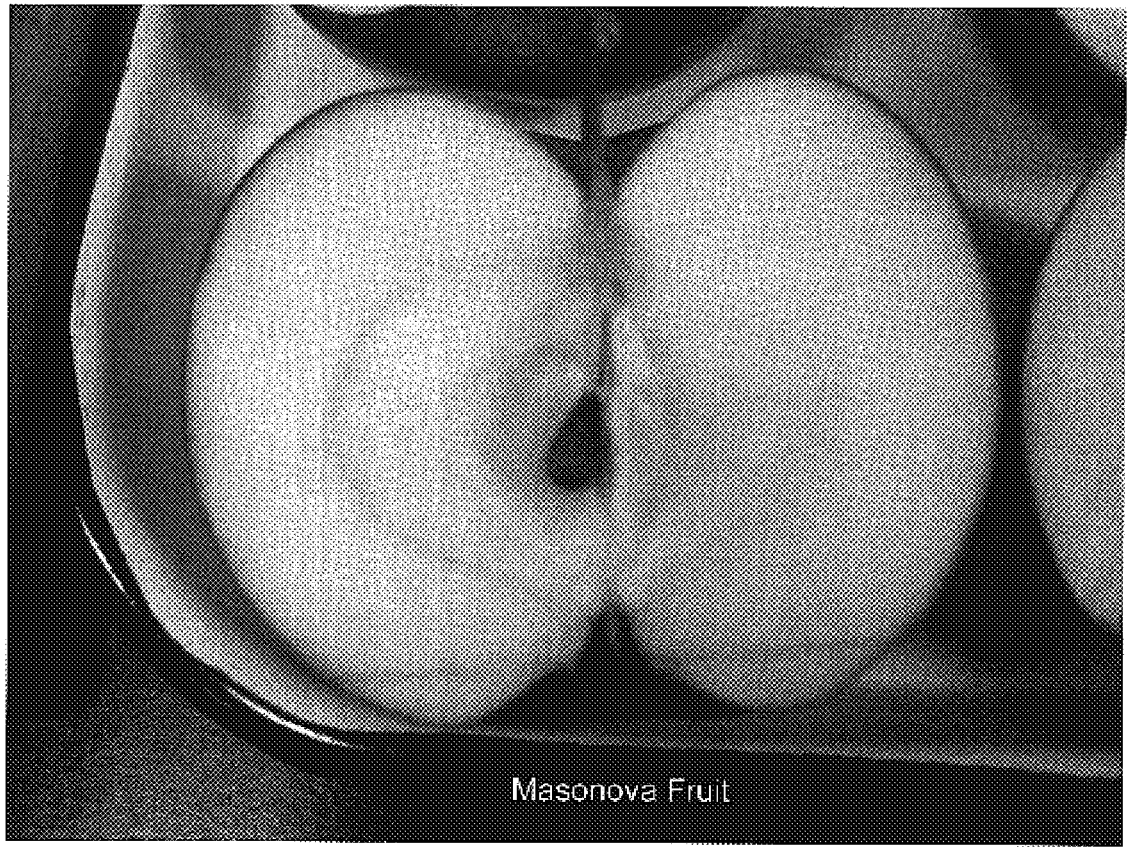
FIG. 6 shows a close-up view of a cross-section of a 'Masonova' apple.
Figure 7A:
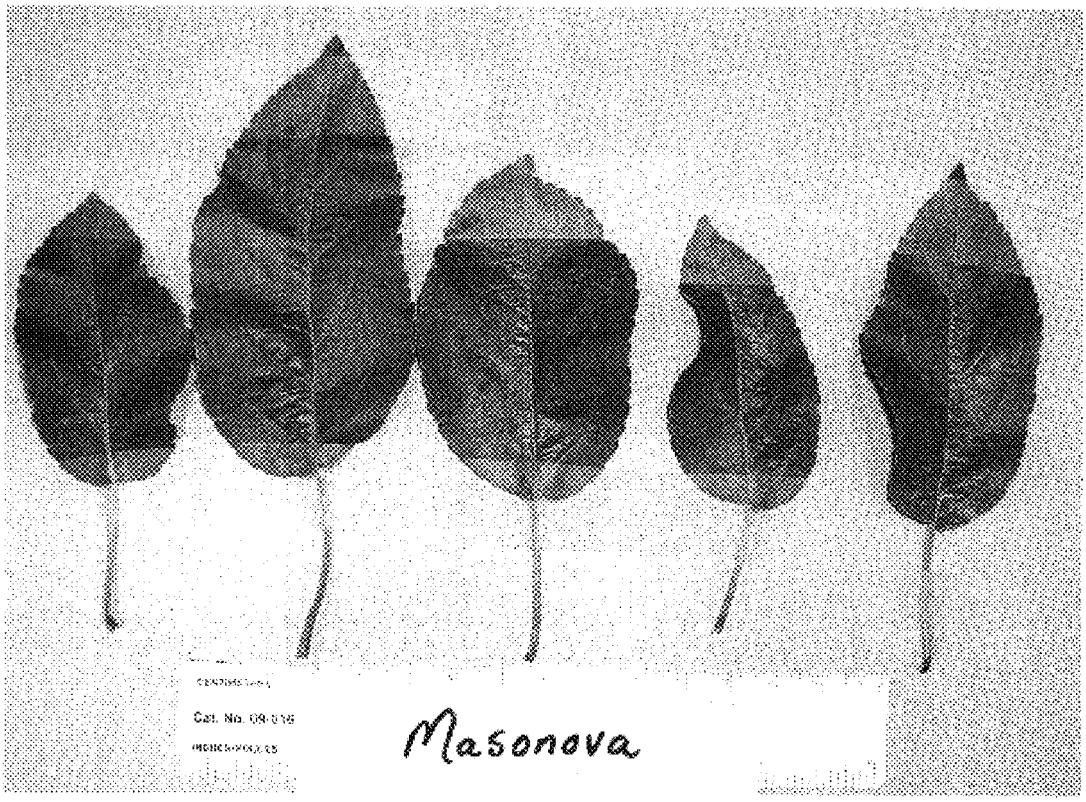
FIGS. 7A and 7B show one side of 'Masonova' leaves.
Figure 7B:
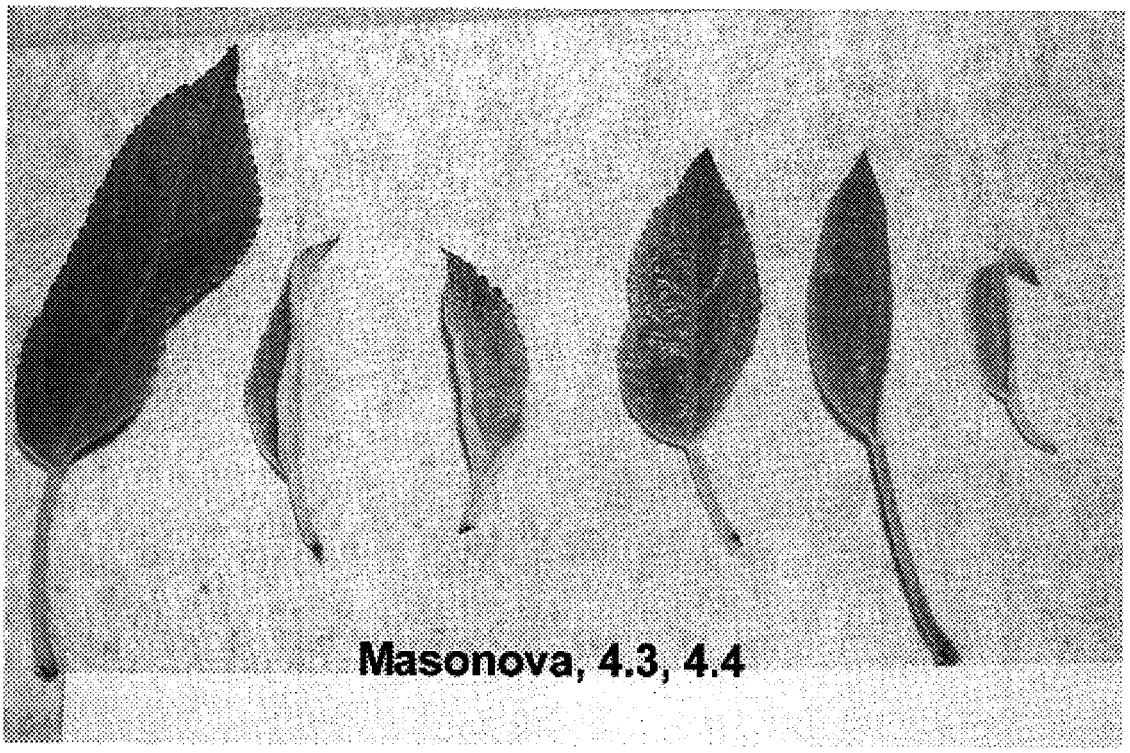
Figure 8:
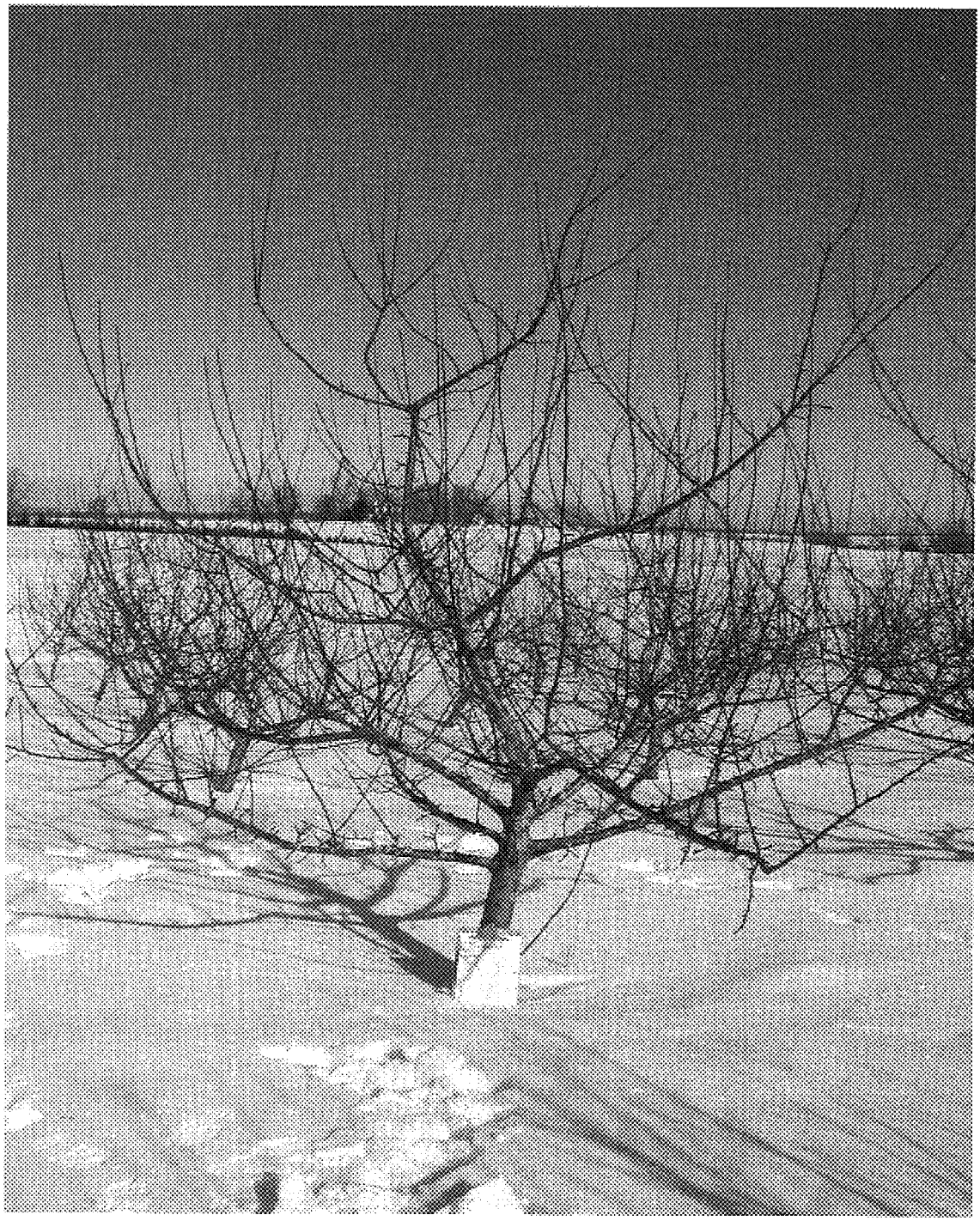
FIG. 8 shows 'Masonova' tree during winter.
Figure 9:
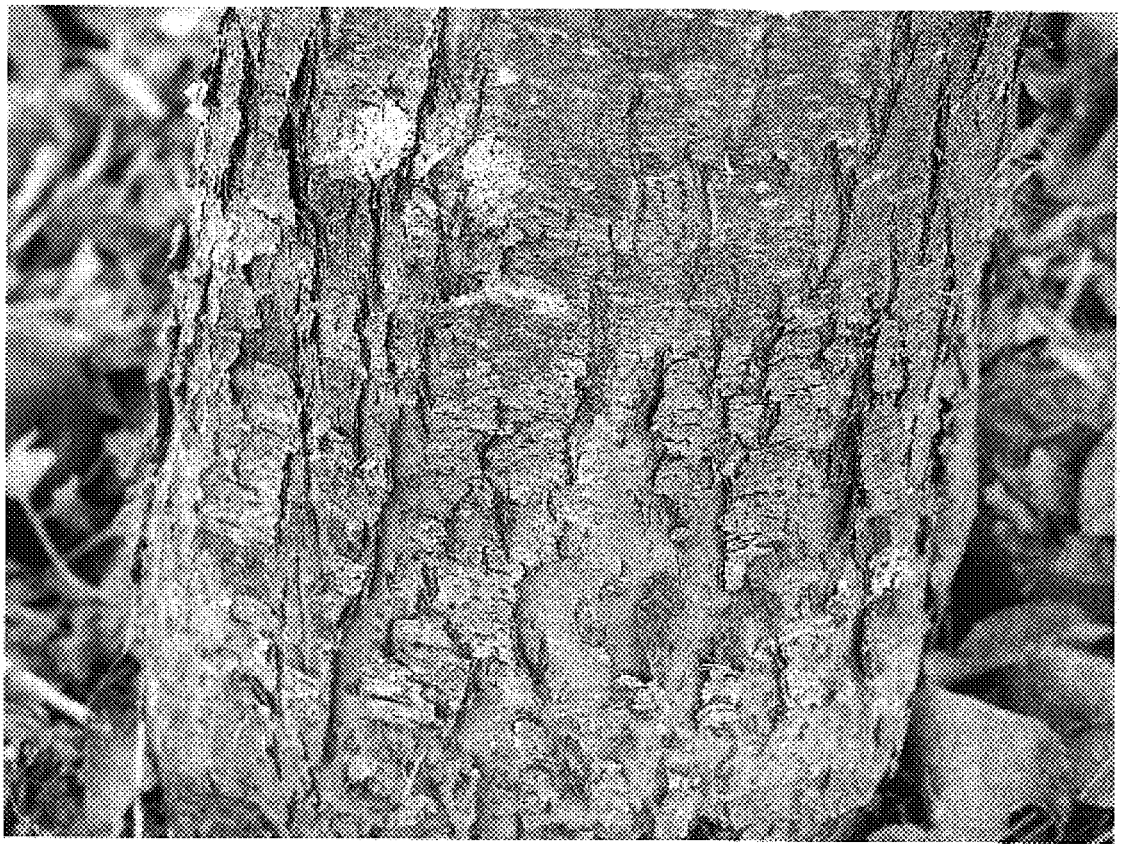
FIG. 9 shows 'Masonova' tree bark.

Trunk bark texture: Thin, flaky, with longitudinal cracks (see FIG. 9.).

Trunk bark color: Brown (RHS 166A).

Patches or other markings: Lenticels present on trunk (horizontal) whitish in color.

*Primary branches.*—Moderate to strong branches; the angle of the fruit bearing branches is less than 90° and the major fruit load is predominantly borne on spurs.

*Branch color.*—One-year old branches are brown-red (RHS 187A) in color, while two-year old branches are brown (RHS 166A) in color.

*Branch pubescence.*—One year old shoots have absent to very sparse pubescence on the upper half.

*Thickness.*—Dormant one-year old shoot have mean thickness of 5.3 mm, with a standard deviation of 0.72.

*New growth bark.*—One year old shoots have moderately shiny bark and are brown (RHS 187A) in color.

*Branch lenticels.*—One year old shoots have few lenticels on the upper half, the lenticels have a low density, approximately 4–6 per square inch; typical examples of which measured about 1.27 mm in diameter; beige brown (RHS 165D) in color.

*Internodes.*—Average internode length is about 24.3 mm on a one-year old shoot.

*Bearing.*—Heavy bearing tree.

*Hardiness.*—At least Zones 5b (Canada).

*Disease resistance.*—Field immune to scab (*Iventuria inaequalis*).

Leaves:

*Size.*—Small to medium.

*Length.*—About 49.6 mm to about 87.7 mm, averaging about 66.9 mm.

*Width.*—Mean 35.8 mm, with a standard deviation of 4.85.

*Margin.*—Crenate.

*Tip shape.*—Acuminate.

*Color.*—Upper leaf surface is green (RHS 143A), lower leaf surface is yellow-green (RHS 147C); vein color is yellow-green (RHS 147C).

*Petiole.*—About 34.4 mm long; about 1.92 mm in diameter, and red-purple (RHS 60B).

*Pubescence.*—Slight. The length, width, thickness and other measurements were obtained from observations of ten typical leaves in 2003.

*Shoot tip leaves.*—Concave in cross section, with sparse pubescence on the upper side. The lower side of the shoot tip leaves is green with no secondary coloration.

Flowers:

*Size.*—Single flowers, 4.3–5.5 cm, typical flower measuring about 5.0 cm across.

*Color.*—Unopened bud: medium pink to dark pink (RHS 65A). Opened flower: upper surface of the petals when the flower is fully open is light blue pink on inner surface of petals (RHS 62B); blue pink on outer surface of petals (RHS 65B).

*Flower bud.*—Length 4.4 mm, width 1.27 mm.

*Petals.*—5 petals per flower; orbicular in shape that touch an overlap; mean width 18.3 mm, with a standard deviation of 1.16; mean length 20.8 mm, with a standard deviation of 1.23.

*Bloom season.*—Seasonal flower development classified as very late; full bloom observed on Jun. 8, 2003.

Fruit: (Observations from a sample of typical fruit in 2003.)

*Size.*—Medium; mean diameter of 7.29 cm, with a standard deviation of 0.40.

*Form.*—Asymmetrical and flat globose; no ribbing; eye is medium in size with an open aperture.

*Stalk cavity.*—Pronounced; broad and medium in depth; mean width 3.7 cm, with a standard deviation of 0.14.

*Eye basin.*—Deep and medium in width; mean depth 6.44 mm, with a standard deviation of 0.99, about 3.0 cm wide.

*Stem.*—Medium in length and thickness; typical average observed in 2003, about 18 mm long and 1.9 mm in diameter; green (RHS 162B) in color.

*Locules.*—Closed.

*Skin.*—Surface is smooth with no bloom and some waxiness.

*Lenticels.*—Slightly prominent and small in size.

*Color.*—General color effect: Dark Red. Ground color: Creamy white (RHS 18C). Overcolor: Very high amount of dark red in a striped blush pattern (RHS 187B). Russetting: None.

*Fruit properties at maturity* (*based on 10 fruit tested in 2006*).—Firmness: Moderate, about 10.13–12.85 kg, averaging about 10.52 kg. (Fruit in storage for 10 weeks). Texture: Fine. Soluble solids: About 13.0%, averaging about 13.0%. Flavor: Mild, sweet, subacid. Juiciness: Moderate. Flesh color: Ivory with some green and red venation surrounding the core (RHS 158C). Flesh browning: Absent to very weak one hour after being cut. Aroma: Strong, ripe apple.

*Core.*—Core line is absent to very weakly distinct; Median bundle area shape, typical in circular about 36 mm long and about 36 mm wide.

*Seed.*—Brown and normal in shape at maturity; about 2–3 seeds per cell, normal shaped; about 8.26 mm long and about 4.33 mm wide; brown (RHS 177A) in color.

*Fruit production.*—First picking date in October in 2003 was about 10th, and last picking date was about same; average production is 400–500 lbs. of fruit per tree.

*Storage.*—Fruit remains fresh at room temperature for 10 days, and can be stored up to 180 days in air storage at 3–4° C.

*Usage.*—Dessert apple, juice or sauce.

Reproductive organs:

*Stamen.*—Arranged in a row; 20 stamens, each about 8.17 mm long and green (RHS 142B) in color.

*Anthers.*—Yellow (RHS 2B).

*Pollen.*—(RHS) in color.

*Pistil.*—Stigma is about 6.60 mm long; 1 styles, at base, and green (RHS 142B) in color. 'Masonova' is self sterile. Potential pollen donors in an orchard setting could be the scab resistant cultivars Nova Spy, Liberty and Gold Rush (unpatented). Potential pollen donors in an orchard setting for scab susceptible cultivars include Cortland (unpatented), Red Delicious, and Honeycrisp (U.S. Plant Pat. No. 7,197).

The following is a comparison of some characteristics of the 'Masonova' apple variety to the reference varieties 'Novaspy' and 'Liberty'.

'Masonova' produces moderately vigorous, upright trees with moderate to strong branches; the angle of the fruit bearing branches is +/−90° and the major fruit load is predominantly borne on spurs. By contrast, the branches of 'Liberty' have a spreading habit and those of 'Novaspy' are weeping. Fruit bearing occurs on both the spurs and shoots for 'Novaspy'. 'Masonova' has stronger branches and wider leaves than the reference varieties. Dormant one year old shoots of 'Masonova' are thicker, less pubescent and have fewer lenticels than those of either reference variety.

Seasonal flower development is classified as very late for 'Masonova' while it is mid-season for 'Novaspy' and mid-season to late for 'Liberty'. 'Masonova' flowers are single with orbicular shaped petals that touch an overlap, while petal shape is ovate to oblong for 'Novaspy' and ovate for 'Liberty'. The color of the flower buds of 'Masonova' is a lighter blue pink than those of the reference varieties.

'Masonova' produces medium sized fruit that are asymmetrical and flat globose in shape with a pronounced eye basin and stock cavity whereas 'Novaspy' produces large fruit which is truncate conical in shape. In comparison to the fruit of the reference varieties, 'Masonova' has a larger eye aperture, deeper eye basin, wider stalk cavity and more over color of the skin than the reference varieties.

The color of the fruit flesh for 'Masonova' is ivory with some green and red venation surrounding the core while it is cream for 'Novaspy' and white for 'Liberty'. Browning of the fruit flesh is absent to very weak for 'Masonova' one hour after being cut, moderate for 'Novaspy' and strong for 'Liberty'. The fruit of 'Masonova' has softer flesh than the reference varieties. The texture of the flesh is fine for 'Masonova' while it is coarse for 'Novaspy.'

Table 1 quantifies some differences between 'Masonova' and the reference varieties.

TABLE 1

Comparison table for 'Masonova'

| | 'Masonova' | 'Novaspy'* | 'Liberty'* |
|---|---|---|---|
| Thickness of dormant one-year old shoot (mm) | | | |
| mean | 5.3 | 3.8 | 4.8 |
| std. deviation | 0.72 | 0.48 | 0.59 |
| Leaf width (mm) | | | |
| mean | 35.8 | 49.9 | 52.8 |

TABLE 1-continued

Comparison table for 'Masonova'

| | 'Masonova' | 'Novaspy'* | 'Liberty'* |
|---|---|---|---|
| std. deviation | 4.85 | 6.42 | 5.75 |
| Petal width (mm) | | | |
| mean | 18.3 | 16.6 | 15.6 |
| std. deviation | 1.16 | 0.70 | 0.52 |
| Color of flower buds (RHS) | 65A | 63B | 63B |
| Color of petals (RHS) | | | |
| inner side | 62B | 62C | 62B |
| outer side | 65B | 63C | 65A |
| Fruit diameter (cm) | | | |
| mean | 7.29 | 7.78 | 7.07 |
| std. deviation | 0.40 | 0.45 | 0.46 |
| Depth of fruit eye basin (mm) | | | |
| mean | 6.44 | 5.83 | 4.51 |
| std. deviation | 0.99 | 1.12 | 0.69 |
| Width of stock cavity (cm) | | | |
| mean | 3.7 | 3.4 | 2.9 |
| std. deviation | 0.14 | 0.37 | 0.18 |

*reference variety

We claim:

1. A new and distinct variety of apple tree, substantially as herein shown and described.

* * * * *

Masonova